United States Patent [19]

Rapoport

[11] Patent Number: 5,371,464
[45] Date of Patent: Dec. 6, 1994

[54] APPARATUS FOR IN-LINE ANALYSIS OF FLOWING LIQUID AND SOLID MATERIALS BY NUCLEAR MAGNETIC RESONANCE

[75] Inventor: Uri Rapoport, Oak Park, Ill.

[73] Assignee: Elbit-ATI, Ltd., Oak Park, Ill.

[21] Appl. No.: 192,190

[22] Filed: Feb. 4, 1994

Related U.S. Application Data

[63] Continuation of Ser. No. 666,349, Mar. 8, 1991.

[51] Int. Cl.$^5$ ............................................. G01R 33/20
[52] U.S. Cl. ................................... 324/306; 324/300
[58] Field of Search ............... 324/300, 308, 306, 318, 324/322; 73/863.41, 863.43, 863.45; 128/653.2

[56] References Cited

U.S. PATENT DOCUMENTS

| | | | |
|---|---|---|---|
| 2,322,018 | 6/1943 | Huber | 73/863.43 |
| 3,564,400 | 4/1968 | Pike | 324/300 |
| 4,215,565 | 8/1980 | Zanker | 73/861.41 |
| 4,341,124 | 7/1982 | Rodgers | 73/861.01 |
| 4,390,957 | 6/1983 | Skarlos | 324/300 |
| 4,417,471 | 11/1983 | Kawai et al. | 73/204.16 |
| 4,531,093 | 7/1985 | Rollwitz | 324/300 |
| 4,564,811 | 1/1986 | Walker | 324/300 |
| 4,638,251 | 1/1987 | King | 324/300 |
| 4,701,705 | 10/1987 | Rollwitz | 324/306 |
| 4,775,836 | 6/1988 | Starewicz | 324/318 |
| 4,862,080 | 8/1989 | Van as | 324/306 |
| 5,045,793 | 9/1991 | Rathke | 324/318 |
| 5,122,746 | 6/1992 | King et al. | 324/300 |
| 5,129,267 | 7/1992 | Nicholls | 324/321 |

FOREIGN PATENT DOCUMENTS 0819657 4/1981 U.S.S.R. ............................ 324/300

Primary Examiner—Louis Arana
Assistant Examiner—Raymond Y. Mah

[57] ABSTRACT

Apparatus for analysis of flowing streams of liquids, flowable solids or mixed liquids and solids by nuclear magnetic resonance techniques. The apparatus is sufficiently small, economical and easy to operate so that it is useful for making measurements in applications such as the production of foods and the like.

6 Claims, 2 Drawing Sheets

APPARATUS FOR IN-LINE ANALYSIS OF FLOWING LIQUID AND SOLID MATERIALS BY NUCLEAR MAGNETIC RESONANCE

This is a continuation of copending application Ser. No. 07/666,349 filed on Mar. 8, 1991.

BACKGROUND OF THE INVENTION

This invention is related to the analysis of flowing streams of liquids, solids or mixed liquids and solids by nuclear magnetic resonance (NMR). In particular, it is an apparatus that is small enough, economical enough and easy enough to operate so that it is useful for making measurements in applications such as the production of foods and the like.

The analysis of materials using NMR requires a region of space containing a magnetic field that is either extremely uniform in magnetic flux density or else extremely uniform in the spatial gradient of magnetic flux density. In such a region, a sample to be analyzed is subjected to a short pulse of electromagnetic energy at a predetermined frequency that is a function of the ions to be analyzed and of their chemical bonding. The pulse is coupled to the sample by a surface coil. A typical pulse duration is of the order of fifty microseconds, although the pulse width that is chosen is a function of the characteristic relaxation time of the material being analyzed. The magnetic field causes the dipole moments of the constituents of the sample to become aligned along lines of magnetic flux. If the field is strong and uniform to a relatively high degree of precision, the dipole moments will be essentially parallel to each other. The electromagnetic energy coupled to the sample changes the alignment of the magnetic dipoles in the sample so as to align them with the net flux, which is the vector sum of the originally applied magnetic field, typically static, and the RF magnetic field associated with the pulse. The relaxation of the dipoles from their re-aligned position back to the original position when the energy coupling is ended produces signals that can be detected and analyzed to identify components of the sample.

Most NMR analysis to date has been done in large and expensive installations that are typically sized to admit a human subject into the region of controlled magnetic fields. Such installations are usually sufficiently complicated to require an operator or operators when the installations are functioning. The result is a large and expensive piece of equipment that is appropriate only for use in a research laboratory or a hospital, and not in a factory or industrial kitchen.

The production of certain foodstuffs would be aided by the ability to use NMR analysis in a pipeline or other such conduit to measure characteristics of flowing liquids, pastes, slurries or solids in powdered or other finely divided form. Continuous or continual analysis of butterfat or cholesterol content would be useful in manufacturing and quality control of dairy products. Fluids containing fats or oils could be analyzed to control processes for manufacturing margarine and similar substances. Doughs and other pasty materials which may be difficult to analyze continuously by other means could be analyzed in-line. These and other such uses, however, require an NMR machine that is suitable for installation and operation in a factory environment and that needs no more than routine operator attention. Such an NMR machine would need one or more surface excitation and pickup coils that are exposed to the flow of material that is to be analyzed, and it would need a flow rate in a sampling area that was related to the relaxation time of the component being tested.

The present invention overcomes the disadvantages of the prior art by providing analysis of flowing streams of liquids by nuclear magnetic resonance with an apparatus that is small enough, economical enough and simple enough to operate so that it is useful for making measurements in applications such as the production of fruits and the like.

Where the flowable material is in a main conduit of a first diameter, a sampling conduct of a second smaller diameter is associated with the main conduit for selectively receiving the flowable material to be analyzed. An NMR device is coupled to the sampling conduit for subjecting the flowable material to the necessary magnetic fields to generate NMR signals and to receive the generated NMR signals for analyzing the flowable materials. A first selectively closable valve is placed in the main conduit for diverting the flowable material to the sampling conduit. If desired, at least one selectively closable valve is placed in the sampling conduit on one side of the coupled NMR device to allow the diverted material to enter the portion of the sampling conduit in the fixed magnetic field for analysis by the NMR device. In one embodiment, the NMR sampling coil is simply wrapped around the sampling conduit for providing the NMR analysis. In another embodiment, the sampling conduit is mounted within the main conduit for receiving a flowable material. The sampling conduit is mounted in the main conduit in a fixed magnetic field such that at least a portion of the sampling conduit is within the magnetic field. The sampling conduit is mounted in the main conduit with a non-metallic, non-magnetic base member coupling the main conduit and the sampling conduit for holding the sampling conduit centered within and parallel to the main conduit. The base member is elongated in the direction of material flow and has a shape such as an ovate cross-section to reduce resistance to the material flow in the main conduit. A coil encircles the flowable material in the sampling conduit with its elongated axis parallel to the direction of the material flow so as to cause a concentrated magnetic field in the flowable material within the sampling conduit. Electrical conductors are embedded in the base and couple the coil to the NMR device for enabling the flowable material to be subjected to the NMR pulse energy and for coupling the generated NMR signals to the NMR device.

In another embodiment, the coil is mounted in the sampling conduit with its elongated axis perpendicular to the material flow. A non-metallic, non-magnetic elongated support for the coil allows the flowable material in the sampling conduit to be sufficiently close to one side of the coil to be excited by the RF pulsed energy and sufficiently far from the other side of the coil to be substantially unaffected by the RF pulsed energy so as to minimize the generation of NMR signals of opposite phase. The mounting device for the coil comprises a non-magnetic, non-metallic elongated support for the coil extending perpendicular to the longitudinal axis of the sampling tube for supporting the coil adjacent to the flow of material in the sampling tube. A non-metallic, non-magnetic base is attached to the support and the sampling conduit such that the material flows sufficiently close to only one side of the coil on the elongated support to be excited by the RF pulsed energy and on each side of the base sufficiently far from the coil to be substantially unaffected by the RF pulsed energy. Thus the base is in the general shape of a T having arcuate surfaces connecting each end of the horizontal arm of the T to the base of the T, the horizontal portion of the T being attached to the elongated support and the base of the T being attached to the sampling conduit. Both the elongated support and the base have a shape, such as an ovate cross-section, to reduce resistance to material flow in the sampling conduit.

In another embodiment, the sampling conduit of a second smaller diameter is associated with the main conduit of a larger diameter for selectively receiving the material. A test conduit is rotatably coupled to the sampling conduit for receiving the material. An NMR device is coupled to the test conduit for subjecting the flowable material therein to a fixed and a variable magnetic field to generate NMR signals and receive the NMR signals for analysis of the flowable material. The test conduit is rotatable with the material flowing therein during subjection of the material to the fixed and variable magnetic fields to correct for irregularities in the magnetic fields.

Thus, it is an object of the present invention to provide an apparatus for performing NMR analysis on flowing materials.

It is a further object of the present invention to provide an apparatus for measurement of characteristics of flowing materials in a factory environment using NMR.

It is yet another object of the present invention to provide an apparatus for making NMR measurements on liquids that are flowing in a conduit.

It is still another object of the present invention to provide an apparatus for NMR measurements on divided solid materials that are flowing in a conduit.

It is also an object of the present invention to provide an apparatus for continual sampling of materials from a flowing stream of materials in a conduit and testing properties of those materials by NMR analysis.

Other objects will become apparent in the course of a detailed description of the invention.

SUMMARY OF THE INVENTION

An apparatus for performing on-line NMR analysis of flowing fluids-including liquids, slurries, pastes and divided solids includes a surface-pickup coil that is disposed in or near the fluid to make measuring contact with the fluid in a main conduit in which the fluid is flowing or in a sampling conduit in which the fluid either is flowing or is stationary but has recently been flowing. The region containing the surface coil is subjected to an extremely uniform static magnetic field. The surface pickup coil or a similar coil used only for excitation is excited with a pulse of RF electric current of a predetermined frequency and time duration to align precession axes of magnetic dipoles of selected materials in the fluid, and the surface pickup coil then detects signals from relaxation of the dipoles to their original positions. These signals are associated with the selected materials in the fluid and can be interpreted to identify these materials and to measure quantities of these materials in the flowing streams from which they were sampled. To do so, the signals are taken to an NMR analyzer which processes them to obtain a free-ion decay curve, a decay spectrum, or both. The sampling conduit may be coupled to the main conduit to selectively receive material diverted from the main conduit. In another embodiment, the sampling conduit may be centered in the main conduit along and parallel to the main conduit elongated axis. In such cases, the coil may be wound around the test tube with its elongated axis parallel to the axis of the test tube or with its axis perpendicular to the axis of the test tube. In still another embodiment, the test tube is rotatable while analyzing a sample in a sample conduit so that the process is a continuous analysis of the flowable materials.

BRIEF DESCRIPTION OF THE DRAWINGS

These and other objects of the present invention will be more fully understood in conjunction with the accompanying drawings in which like numbers indicate like components and in which.

DETAILED DESCRIPTION

Figure 1:
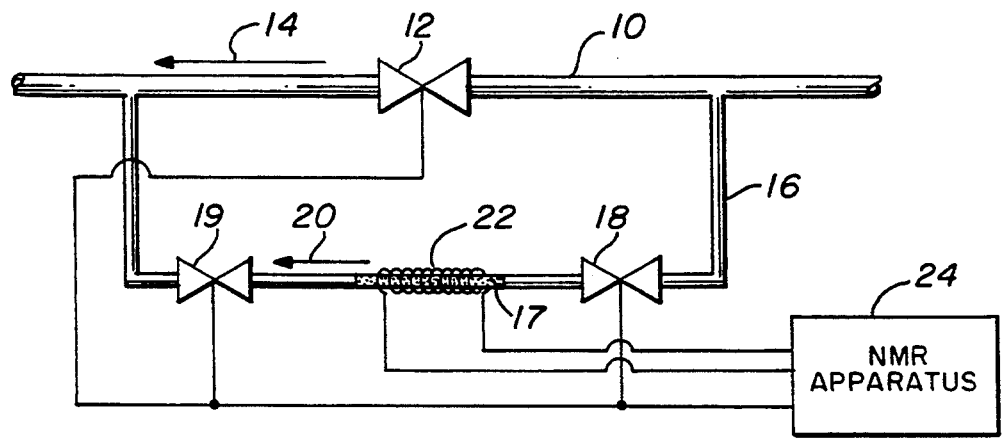
FIG. 1 is a diagrammatic representation of an apparatus for the practice of the present invention.

FIG. 1 is a diagrammatic representation of an apparatus for the practice of the present invention. In FIG. 1, a main conduit 10 carries a flow of liquid, paste, slurry or divided solid through a valve 12 in the direction of an arrow 14. The valve 12 is optional, but it may be useful in directing flow through a sampling conduit 16 and controllable valves 18 and 19 in the direction of an arrow 20. The sampling conduit 16 has at least a portion 17 thereof that is placed in a magnetic field and that is conveniently sized to fit a surface coil 22 which is connected to an NMR apparatus 24. The conduit portion 17 may be formed of any nonconductive material such as plastic. The sampling conduit portion 17 can be sized to fit surface coil 22 without putting a limit on the size of the main conduit 10 and hence on the quantity of material that flows in the main conduit 10. The positioning of the sampling conduit 16 and the valves 18 and 19 makes it possible to control the flow rate in the sampling conduit 16 and hence, the flow through the conduit portion 17 surrounded by surface coil 22. They also make it possible to take a sample and hold it stationary during a period of analysis, which typically takes in the order of seconds to gather data. The NMR apparatus 24 controls the operation of valves 12, 18 and 19 and also analyzes the sample in conduit 16.

Figure 2:
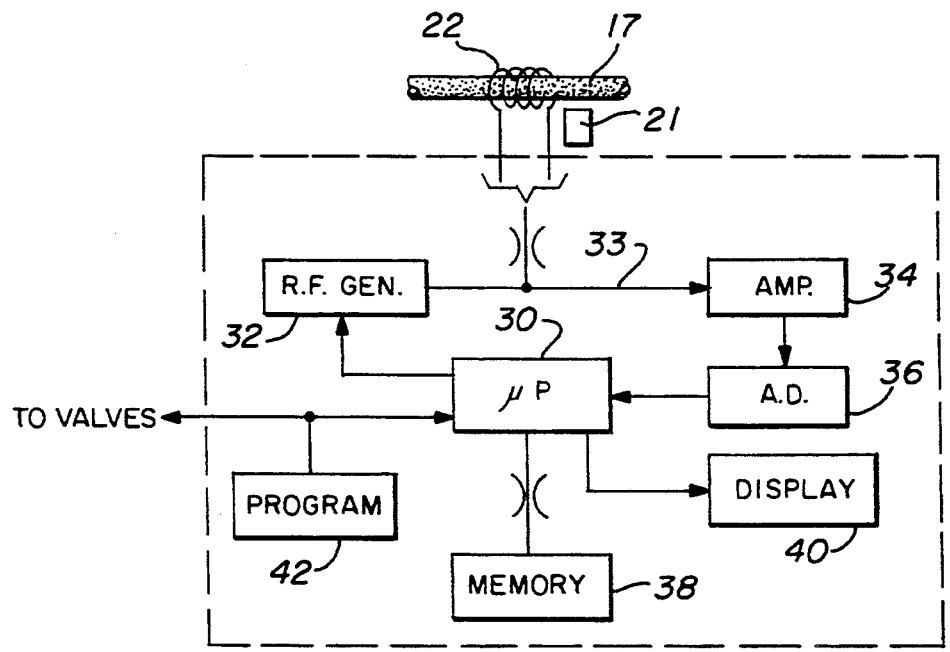
FIG. 2 is a functional block diagram of a portion of the apparatus of FIG. 1.

FIG. 2 is a functional block diagram of the surface coil 22 and NMR apparatus 24 of FIG. 1. In FIG. 2, the surface coil 22 is disposed in a magnetic field generated by magnet 21 and encloses a flowing sample of material in conduit 17 that is to be analyzed by NMR techniques. The surface coil 22 is connected to the NMR apparatus 24, which is controlled by a microprocessor 30. A signal from the microprocessor 30 gates an RF generator 32 that applies pulsed electromagnetic energy to the flowing sample in conduit portion 17 through the surface coil 22. After the RF generator 32 is gated off by the microprocessor 30, detected NMR signals are taken on line 33 to an amplifier 34 that is connected to an analog-to-digital (A/D) converter 36. In converter 36 the NMR signals are digitized for connection to the microprocessor 30 as is well-known in the art. The microprocessor 30 is connected to the memory 38 and a display 40 and may be programmed or controlled by a program 42. The operation of the NMR apparatus 24 is described in more detail in U.S. Pat. No. 4,875,486, which is assigned to the assignee of the present invention and which is incorporated here by reference as if set forth fully. Operation of the NMR apparatus 24 is also facilitated by using as the amplifier 34 a true log amplifier as disclosed in pending U.S. Pat. Ser. No. 403,089, which is also assigned to the assignee of the present invention and which is incorporated here by reference as if set forth fully.

It is well known in NMR analysis that particular compounds that are subjected to a static magnetic field tend to have dipole moments aligned with the magnetic field. The application of a pulse of electromagnetic energy which sets up a magnetic field in a direction different from the direction of the static field changes the alignment of these dipoles to that of the resultant magnetic field. When the pulse is then turned off, the relaxation of the dipoles to their original alignment with the static magnetic field produces signals that can be detected and analyzed for the presence of components in the compound having the particular dipole moments in question.

The application of NMR analysis to measure characteristics of flowing materials requires either that the relaxation of dipoles be substantially complete while the excited flowing material is within range of the surface coil that has excited the dipoles, or else that more than one surface coil be used. The choice between using one coil and using more than one is determined primarily by the answer to the question whether relaxation will be substantially complete while the sample is still within the detection range of one coil. If it will not be, then two coils will be needed. In either case, the procedure is well known in the art.

Figures 3A, 3B:
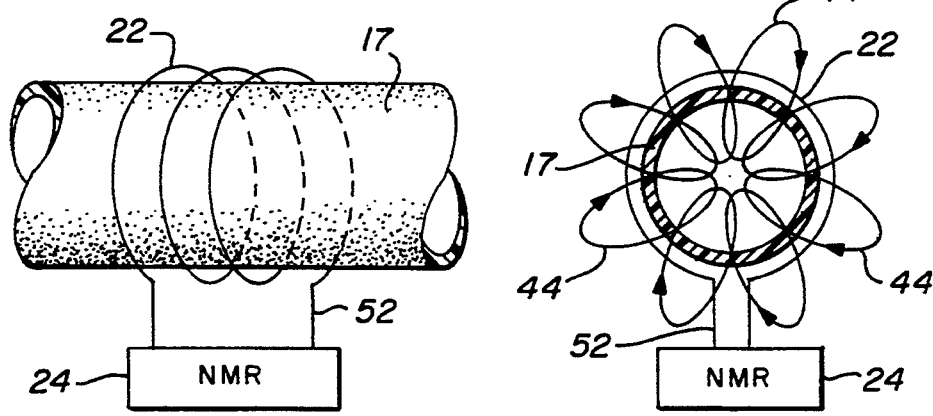
FIG. 3A is a view of an embodiment of a surface pickup coil to be used in the apparatus of FIG. 1.
FIG. 3B is a cross-sectional view of the device in FIG. 3A illustrating the concentration of the magnetic field in the center of the conduit carrying the sample under test.

FIG. 3A is a view of a pickup coil to be used in one embodiment of the apparatus of FIG. 1. In FIG. 3A, the conduit section 17 has flowing therein the material to be analyzed. The coil 22 is wrapped around the conduit 17 with one or more turns as needed to generate RF pulses for exciting the material in conduit 17 and also for picking up the NMR signals that are coupled on lines 52 to the NMR device 34. The coil can be wound about the outside of conduit 17 because it causes a strong magnetic field on the inside of conduit 17 and a weak magnetic field on the outside of conduit 17. This can be seen more clearly in FIG. 3B which is a cross-sectional view of the conduit 17 in FIG. 3A. In FIG. 3B, it can be seen that the coil 22 is wound around the outside of the conduit 17. It will be noted that the flux lines 44 all converge on the inside of conduit 17. Thus, there is a strong magnetic field on the inside of conduit 17 and a weak magnetic field on the outside thereof. The NMR signals generated by the nuclei of the material under test is detected by coil 22 and coupled on lines 52 to the NMR device 24. In FIG. 3A, because the coil 22 is wound about the outside of conduit section 17, it is possible to rotate conduit 17 for providing a more accurate reading as described in commonly assigned co-pending application Serial No. 07/666,576, filed Mar. 8, 1991, and incorporated herein in its entirety by reference. Thus, the embodiment illustrated in FIG. 3A allows the sampled material to be non-rotating within the magnetic field or rotated by the rotation of conduit 17.

Figure 4A:
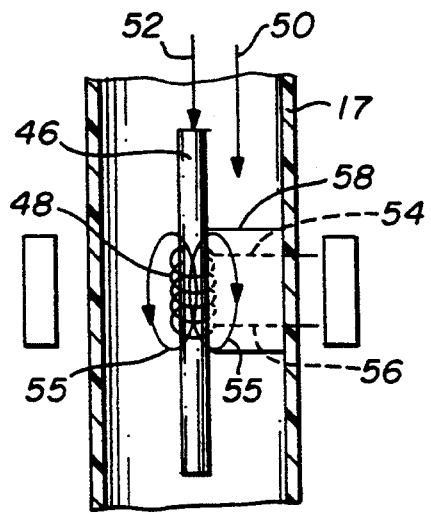
FIG. 4A is a sectional view of an alternate embodiment of an apparatus for the practice of the present invention.
Figures 4B, 4C:
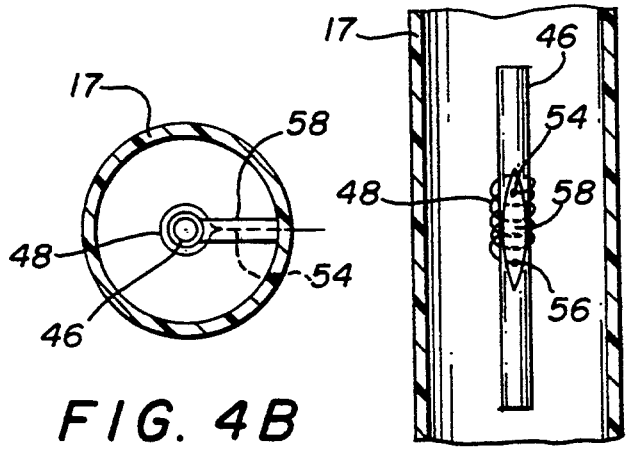
FIG. 4B is a top view of the device in FIG. 4A.
FIG. 4C is a side view of the device in FIG. 4A.

FIG. 4A is a cross-sectional view of an alternate embodiment of a device for sampling a continuously moving fluid in a conduit. In the cross-sectional view illustrated in FIG. 4A, it can be seen that a small internal conduit 46 is mounted on the inside of sampling conduit 17 at the center thereof with a mount 58. Conduit 17 could, of course, be the main conduit and smaller conduit 46 could be called the sampling conduit. The mount 58 is shaped in the elongated direction as an oval, as can be seen best in FIG. 4C. The oval shape allows fluid to pass thereby unimpeded or at least with a minimum of flow resistance. A coil 48 is wrapped around internal conduit 46 and has its output leads 54 and 56 passing through the mount 58 to the outside of the conduit 17 where they can be coupled to the NMR device 24 illustrated in FIGS. 1 and 2. Thus, as the material flows into conduit 17 in the direction of arrow 50, a portion of the fluid follows the direction of arrow 51 into the internal conduit 46 where it can be analyzed by typical NMR methods. FIG. 4B is a top view of the device illustrated in FIG. 4A and illustrates the minimum interference with fluid flow by the mount 58 and illustrates the relationship of the coil 48, the internal conduit 46 and the mounting bracket 58. Thus, the device shown in FIGS. 4A, 4B and 4C can be utilized for a stationary conduit 17 to be used to take NMR measurements of a sample. It cannot be used where it is desired to rotate the tube or conduit 17.

Figure 5A:
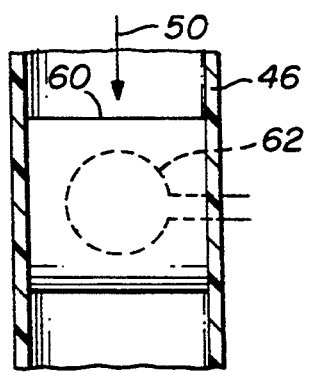
FIG. 5A is a perspective view of a second alternate embodiment of an apparatus for the practice of the present invention.
Figure 5B:
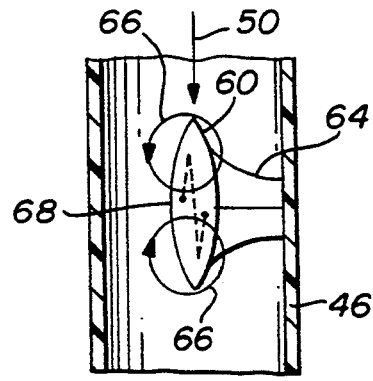
FIG. 5B is a side view of the device of FIG. 5A.
Figure 5C:
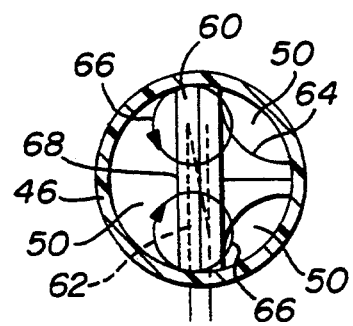
FIG. 5C is a top view of the device of FIG. 5A.

FIGS. 5A, 5B and 5C illustrate a second alternate embodiment of a conduit which contains a coil for providing signals to an NMR device. FIG. 5A is a side view of an alternate device for mounting the coil in the conduit 17. In FIG. 5A the coil is mounted in the tube such that its axis is perpendicular to the flow of the fluid. In such case, the coil 62 is positioned in a mounting bracket 60 to shield the coil 62 from the fluids. It may be made similar to mount 58 in FIG. 4A, 4B and 4C of glass, plastic and other nonmagnetic and nonmetallic materials. In such case, it is not desirable to allow the fluid to pass on either side of the coil 62 equidistant from the coil. The reason is that the flux lines 66, as shown in FIG. 5B, concentrate in density near the center of the coil 62. Because the flux enters one side of the coil and exits the other, a reverse polarity is encountered when NMR signals from the material on either side of the coil are detected. They are of opposite phase. Therefore, it is desirable that the material interact with coil 62 on only one side thereof. Thus, the coil 62 is mounted on the side of mounting bracket 60 away from the mounting base 64 as shown in FIG. 5B. The distance from the front 68 of the mounting bracket 60 to the coil 62 is very small, thus allowing free interaction of the fluid in the heavy density magnetic field lines 66. However, the back distance from coil 62 to the outside 64 of mounting bracket 60 is considerably larger and thus, as illustrated in FIG. 5C, the lines of flux are already breaking up in those areas and thus are much less dense. Consequently, there is less interaction between the nuclei of the materials in flow through areas designated by the numeral 50 on each outside 64 of base 60 than there is in the area 50 in front of side 68 of mounting bracket 60. Again, mounting bracket 60 is formed with an oval cross section in the vertical direction as illustrated in FIG. 5B to allow the fluid entering conduit 17 in the direction of arrow 50 to pass freely over the mounting bracket 60. In like manner, the portion of mounting bracket 60 including outside 64 is also oval shaped in cross section so as to allow a free fluid flow in the passages 50 on either side thereof.

Figure 6:
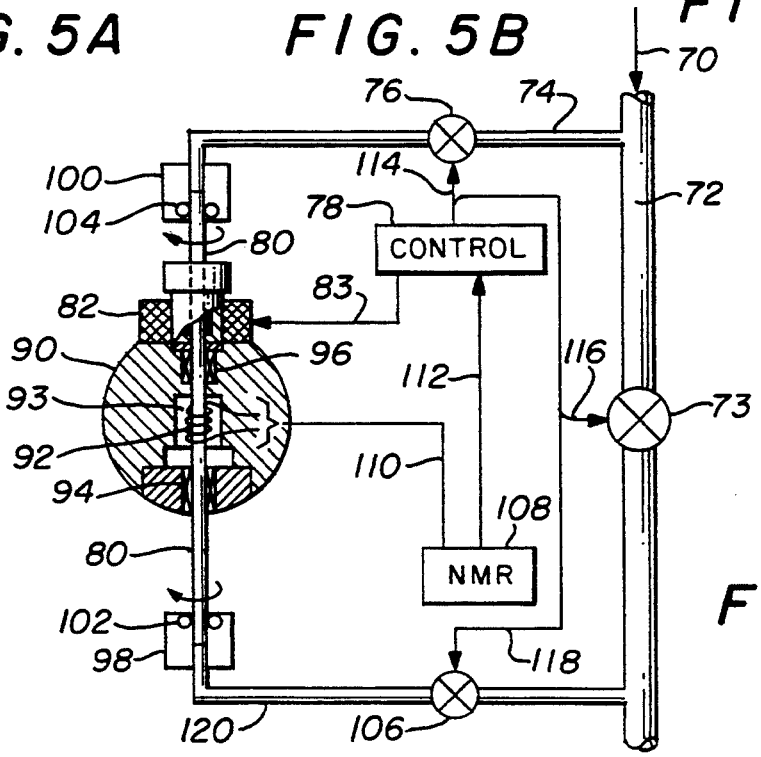
FIG. 6 is a diagrammatic representation of a flow through in-line NMR device.

FIG. 6 is a diagrammatic representation of a flow through in-line NMR apparatus which can perform NMR tests with a rotating test tube. In FIG. 6, the incoming fluid 70 passes through conduit 72 and valve 73 to some production facility where the fluid would be utilized. The fluid may be of the type referred to previously which requires periodic analysis and testing. In such case, a sampling conduit 74 diverts some of the fluid through a closable valve 76 to a rotating test tube 80. The manner in which test tube 80 is rotated is disclosed in detail in commonly assigned copending application Ser. No. 07/666,576, filed Mar. 8, 1991, which is incorporated herein by reference in its entirety. Generally speaking however, a motor 82 drives a hollow shaft 85 to which the test tube 80 is frictionally coupled. The motor 82 is controlled by signals on line 83 from a control unit 78 which may be a program. The test tube passes through a cavity 93 in a magnet 90 with a coil 92 located in the cavity 93. Self-lubricating bearings 94 and 96 support the test tube 80 for rotation. Coupling units 98 and 100 have self-lubricating seals such as Teflon seals 102 and 104 to prevent fluid leakage in the coupling units 98 and 100. Valve 106 in output line 120 may be opened and closed as needed to subject the sample to the NMR testing. An NMR device 108 is coupled on line 110 to the coil 92 in cavity 93 to pulse the coil and to detect the NMR signals generated by the material under test. The NMR device 108 includes a computer which communicates with the program 78 to control valves 73 with signals on line 116, 76 with signals on line 114 and 106 with signals on line 118. It also controls the speed of the motor 82 with the signals on lines 83 to rotate the test tube 80 at the desired speed. With valves 76 and 106 open and valve 73 closed, a continual flow of fluid through test tube 80 can occur, thus having the NMR testing occur as the material is passing through the sampling conduit 74. Clearly, it would not be necessary to rotate test tube 80 in the schematic representation illustrated in FIG. 6. If more accurate readings are required, then the test tube can be rotated as indicated.

Thus, there has been disclosed a novel system for analysis of flowing streams of liquids, solids or mixed liquids and solids by nuclear magnetic resonance. The pulsing and detecting coil can be wrapped around the outside of a conduit carrying the fluid, it can be wrapped around a conduit within a larger conduit that is carrying the fluid, it may be positioned with its axis perpendicular to the fluid flow with the fluid in operative relationship with only one side of the coil to reduce errors and includes a flow through system in which the test tube may be rotatably located in a magnetic field to provide more accurate analysis of the sample under test.

The foregoing specification describes only the embodiments of the invention shown and/or described. Other embodiments may be articulated as well. The terms and expressions used, therefore, serve only to describe the invention by example and not to limit the invention. It is expected that others will perceive differences which, while different from the foregoing, do not depart from the scope of the invention herein described and claimed. In particular, any of the specific constructional elements described may be replaced by any other known element having equivalent function.

I claim:

1. A flow through device for NMR analysis and identification of constituents in a continuously flowable material comprising:

a main conduit of a first diameter for carrying said material to be analyzed;

a sampling conduit of a second smaller diameter associated with said main conduit for selectively receiving a portion of said material to be analyzed without regard to the volume of material carried by the main conduit;

an NMR device coupled to said sampling conduit for subjecting said flowable material to a fixed and a variable magnetic field to generate NMR signals and receiving said generated NMR signals for identifying the constituents of said flowable materials;

means adjacent said sampling conduit for generating a fixed magnetic field through which at least a portion of said sampling conduit passes;

means for generating RF pulse energy;

means associated with said sampling conduit portion subjected to said magnetic field for receiving said RF pulses and exciting said flowable material with a variable magnetic field and detecting said generated NMR pulses;

means coupled to said detecting means for analyzing said detected NMR signals to identify said constituents in said flowable material;

means for mounting said sampling conduit within and parallel to said main conduit for receiving said flowable material;

means for mounting said main conduit in said fixed magnetic field such that at least a portion of said sampling conduit is within said magnetic field;

means for mounting a coil in said sampling conduit with its elongated axis perpendicular to said material flow; and said mounting means allowing said flowable material in said sampling conduit to be sufficiently close to one side of said coil to be excited by said RF pulsed energy and sufficiently far from the other side of said coil to be substantially unaffected by said RF pulsed energy so as to minimize the generation of NMR signals of opposite phase.

2. A device as in claim 1 wherein said coil mounting means comprises:

a nonmetallic, nonmagnetic elongated support for said coil extending perpendicular to the longitudinal axis of said sampling tube for supporting said coil adjacent the flow of material in the sampling tube; and a nonmetallic, nonmagnetic base attached to said support and said sampling conduit such that said material flows sufficiently close to only one side of said coil on said elongated support to be excited by said RF pulsed energy, and ground said base sufficiently far from said coil to be substantially unaffected by said RF pulsed energy.

3. A device as in claim 2 wherein said base is in the shape of T having arcuate surfaces connecting each horizontal end of the T to the base of the T, the horizontal portion of the T being attached to said elongated support and the base of the T being attached to said sampling conduit wherein said elongated support and said base have a shape to reduce resistance to material flow in said sampling conduit.

4. A method of analysis and identification of constituents in a continuously flowable material with an NMR device comprising the steps of:

moving said material to be analyzed in a main conduit having a first diameter;

coupling a sampling conduit having a second smaller diameter in parallel with said main conduit for selectively receiving a portion of said material as a volume to be analyzed without regard to the volume of material carried by the main conduit;

coupling an NMR device to said smaller diameter sampling conduit for subjecting said flowable material to a fixed and a variable magnetic field for generating NMR signals that are used to identify the constituents of said flowable material;

generating a fixed magnetic field through which at least a portion of said sampling conduit passes;

generating pulsed RF energy;

exciting said flowable material with a variable magnetic field caused by said pulsed RF energy to generate said NMR signals;

detecting said NMR signals for use in identifying said constituents in said flowable material;

mounting a coil in said sampling conduit with its elongated axis perpendicular to said material flow; and allowing said flowable material in said sampling conduit to be sufficiently close to one side of said coil to be excited by said RF pulsed energy and sufficiently far from the other said of said coil to be substantially unaffected by said RF pulsed energy so as to minimize the generation of NMR signals of opposite phase.

5. A method as in claim 4 wherein the step of mounting said coil further comprises the steps of:

extending a nonmetallic, nonmagnetic elongated support for said coil perpendicular to the longitudinal axis of said sampling conduit for supporting said coil adjacent the flow of material in the sampling conduit; and attaching a nonmetallic, nonmagnetic base to said support and said sampling conduit such that said material flows sufficiently close to only one side of said coil and said elongated support to be excited by said RF pulsed energy and around said base sufficiently far from said coil to be substantially unaffected by RF pulsed energy.

6. A method as in claim 5 further including the step of forming said base in the shape of a T having arcuate surfaces connecting each horizontal end of the T to the base of the T, the horizontal portion of the T being attached to said elongated support and the base of the T being attached to said sampling conduit and further including the step of shaping said elongated support and said base to reduce resistance to material flow in said sampling conduit.

* * * * *

UNITED STATES PATENT AND TRADEMARK OFFICE
CERTIFICATE OF CORRECTION

PATENT NO. : 5,371,464
DATED : December 6, 1994
INVENTOR(S) : Uri Rapoport

It is certified that error appears in the above-indentified patent and that said Letters Patent is hereby corrected as shown below:

Column 8, line 63, claim 2, delete ", and ground" and insert --adn around --.

Signed and Sealed this

Twenty-fifth Day of April, 1995

Attest:

BRUCE LEHMAN

Attesting Officer

Commissioner of Patents and Trademarks